Figure 1:
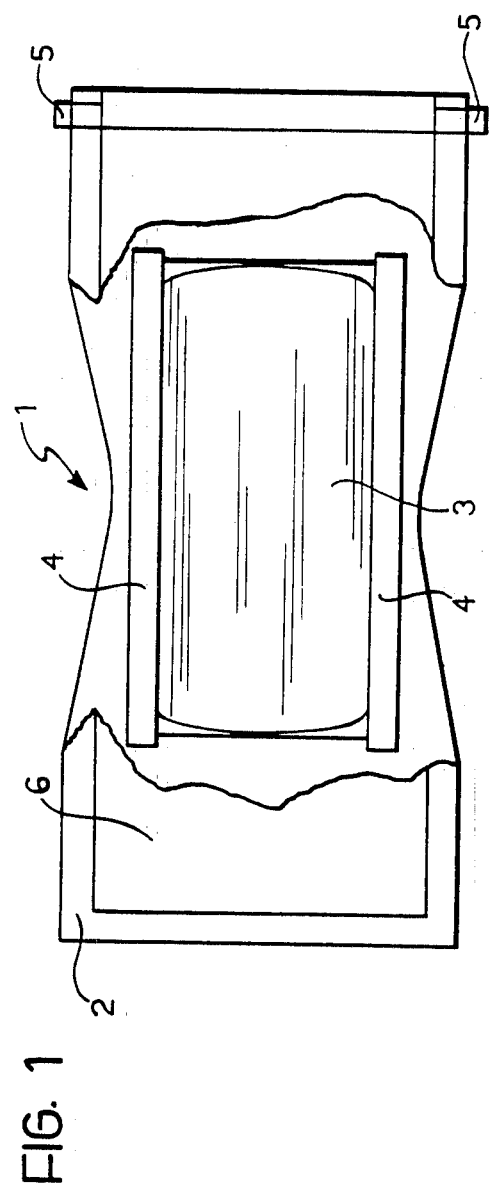

United States Patent [19]

Bianco

[11] Patent Number: 4,572,043

[45] Date of Patent: Feb. 25, 1986

[54] METHOD AND APPARATUS FOR FORMING ELASTIC ELEMENTS UNDER TENSION FROM A CONTINUOUS ELASTIC WEB, PARTICULARLY FOR MANUFACTURING SANITARY PRODUCTS SUCH AS DISPOSABLE DIAPERS AND THE LIKE

[75] Inventor: Carlo Bianco, Pescara, Italy

[73] Assignee: Fameccanica S.p.A., Italy

[21] Appl. No.: 660,193

[22] Filed: Oct. 12, 1984

[30] Foreign Application Priority Data

Oct. 12, 1983 [IT] Italy .................................. 68052 A/83

[51] Int. Cl.[4] ........................ B32B 31/10; B32B 31/18
[52] U.S. Cl. .......................................... 83/18; 83/154; 83/175; 83/343; 156/164; 156/229; 156/494; 156/519
[58] Field of Search ............... 156/164, 161, 229, 176, 156/178, 264, 265, 433, 494, 519; 83/18, 154, 175, 343

[56] References Cited

U.S. PATENT DOCUMENTS

| | | | |
|---|---|---|---|
| 4,081,301 | 3/1978 | Buell | 156/164 |
| 4,297,157 | 10/1981 | Van Vliet | 156/164 |
| 4,364,787 | 12/1982 | Radzins | 156/519 |
| 4,397,704 | 8/1983 | Frick | 156/519 |
| 4,523,969 | 6/1985 | Spencer | 156/164 |
| 4,525,229 | 6/1985 | Suzuki et al. | 156/164 |

Primary Examiner—Michael Ball
Attorney, Agent, or Firm—Sughrue, Mion, Zinn, Macpeak & Seas

[57] ABSTRACT

A supply source of continuous elastic web and a support for the fixing of elastic elements are provided. On the support, which is normally constituted by a rotary drum, there are located at least one clamping element fixed to the support itself and a further clamping element which is movable relative to the fixed element between first and second positions. The distance between the fixed element and the movable element in the second position is less than the distance between the two elements in the first position and is substantially equal to the length of the tensioned elastic elements which it is desired to form. The free end of the continuous elastic web is clamped in the movable clamping element when this element is in its first position. There is thus produced, simultaneously and substantially continuously:

a relative movement between the supply source and the support in the direction of alignment of the clamping elements so as to cause the supply of the continuous web to the fixed clamping element;

the translational movement of the movable clamping element from its first position to its second position at a velocity less than the velocity of the movement between the web supply source and the support, and the supply of the web from the source at a velocity less than the difference between the velocity of the relative movement between the source and the support and the velocity of the translation of the clamping element between the first and second positions. When the movable clamping element reaches the second position, the web is clamped by the fixed clamping element whereby a piece of web extends between the fixed clamping element and the movable clamping element in a state of longitudinal tension the degree of which is determined by the velocity difference and the supply velocity of the web. Finally, the web is cut in the region between the fixed clamping element and the supply source, so as to separate the said piece from the body of the web and define one of the tensioned elastic elements, and to form a new free end of the web iself.

11 Claims, 7 Drawing Figures

METHOD AND APPARATUS FOR FORMING ELASTIC ELEMENTS UNDER TENSION FROM A CONTINUOUS ELASTIC WEB, PARTICULARLY FOR MANUFACTURING SANITARY PRODUCTS SUCH AS DISPOSABLE DIAPERS AND THE LIKE

TEXT OF THE DESCRIPTION

The present invention relates to a method for forming elastic elements under tension from a continuous elastic web.

The invention is preferably applied to the manufacture of sanitary products such as, for example, disposable diapers for infants or incontinent adults.

In such diapers, tensioned elastic elements are fixed along the longitudinal edges of a sheet of impermeable plastics material which constitutes the outer cover of the product, in order to achieve better adherence of the diaper around a user's legs.

Various methods and apparatus are known for forming and applying elastic elements to disposable diapers and like products.

For example, U.S. Pat. No. 4,081,301 proposes the uniform stretching of a rubber web, the application of adhesive to discrete lengths of this web, and the sticking of this web to a continuous sheet of impermeable plastics material defining the outer cover of the diaper. The web is kept under tension until the adhesive sets and is subsequently cut in the regions free from adhesive. As a result of this cutting, the adhesive-free regions stuck to the sheet of plastic material contract and return to the rest condition.

The main disadvantage of this method arises from the fact that the adhesive-free portions of the web are wasted material since they do not contribute in any way to the elasticity or adherence of the diaper with which they are associated.

U.S. Pat. No. 4,297,157 discloses a method in which a continuous elastic web is tensioned and clamped between two jaws spaced by a distance greater than the final length of the elastic element it is wished to form. After the piece of web between the two jaws is separated from the body of the continuous web, the two jaws are brought closer together until they are at a distance corresponding to the final length. Under these conditions, the piece between the two jaws is stuck to a product such as a disposable diaper.

The main advantage of this method lies in the fact that, before the elastic element can be brought to the length corresponding to the state of tension in which it is applied to the diaper, it is subjected to an initial intense stretching operation ("over-stretching") whereby it is extended to a length typically twice that for the final application. This operation can compromise the elastic characteristics and the integrity of the elastic element, consequently reducing the production yield.

The object of the present invention is to provide a method the type specified above, which does not have the disadvantages described previously and which can be carried out economically on an industrial scale.

According to the present invention, this object is achieved by virtue of a process of the type specified, characterised in that it includes the steps of:
providing a supply source of the web;
providing a support for fixing the elastic elements, having a clamping element fixed to the support and a further clamping element movable relative to the fixed element between a first position and a second position; the distance between the fixed clamping element and the movable clamping element in the second position being less than the distance in the first position and substantially equal to the length of the tensioned elastic elements;
clamping the free end of the continuous web in the movable clamping element in the first position;
causing simultaneously and substantially continuously,
  (a) a relative movement between the supply source and the support in the direction of alignment of the clamping elements so as to cause the supply of the continuous web to the fixed clamping element,
  (b) the translational movement of the movable clamping element from the first position to the second position at a velocity less than the velocity of the relative movement between the supply source and the support, and
  (c) the supply of the web from the source at a velocity less than the difference between the velocity of the relative movement between the source and the support and the velocity of the translation of the movable clamping element from the first position to the second position;
clamping the web in the fixed clamping element when the movable clamping element reaches the second position, in an arrangement such that a piece of web defining one of said elastic elements extends between the fixed clamping element and the movable clamping element in a state of longitudinal tension the degree of which is determined by the velocity difference and the supply velocity of the web, and
cutting the web in the region between the fixed clamping element and the supply source, to separate the tensioned piece from the main body of the web and form a new free end of the web.

By virtue of this characteristic, a method is achieved which allows tensioned elastic elements to be made from a continuous elastic web in a practical, economic and quick manner. To advantage, this process can be carried out on an industrial scale with particular reference to the manufacture of elastic products such as disposable diapers for infants and incontinent adults.

In the currently preferred embodiment, the method according to the invention is characterised in that it includes the steps of:
providing a supply source for the continuous web;
providing a support movable relative to the supply source at a predetermined velocity and carrying associated clamping elements fixed to the support and movable clamping elements, which are aligned in alternation in the direction of movement of the support; each of the movable clamping elements being able to effect a reciprocating translational movement between a first position substantially adjacent the fixed clamping element upstream of the movable element in the direction of movement of the support, and a second position intermediate the upstream fixed clamping element and the downstream fixed clamping element in the direction of movement;
clamping the free end of the continuous web in one of the movable clamping elements in the first position;
driving the translational movement of the movable clamping element carrying the clamped free end of the web from the first position to the second position at a velocity less than the velocity of movement of the support, simultaneously supplying the continuous web to the support at a velocity less than the difference between the velocity of movement of the support and the translational velocity of the movable element between the first and second positions;

clamping the web in the fixed element located downstream of the movable element in the direction of movement of the support when the movable clamping element reaches the second position, in an arrangement such that a piece of web defining one of the elastic elements extends between the movable clamping element and the fixed clamping element located downstream in a state of tension the degree of which is determined by the velocity difference and the supply velocity of the web;

clamping the web in a further movable clamping element located in the first position downstream of the fixed clamping element in the direction of movement of the support, and cutting the web in the region between the fixed clamping element, separating the tensioned piece from the main body of the web and forming a new free end of the web clamped in the further movable clamping element and defining one of the ends of a new elastic element.

A further subject of the present invention is apparatus for forming tensioned elastic elements from a continuous elastic web, characterised in that it includes:

a rotary drum having first clamping elements fixed to the drum and second movable clamping elements aligned in alternation along the outer surface of the drum; each of the movable elements being able to effect a reciprocating translational movement between a first position substantially adjacent the fixed clamping element located upstream in the direction of movement of the surface of the drum and a second position in which each movable clamping element is located in a position intermediate the fixed clamping elements between which it is interposed at a distance from the fixed clamping element located downstream in the direction of movement of the surface of the drum substantially equal to the length of the elastic elements;

first actuator means which can move the movable clamping elements in a disposition such that, in a predetermined region of the path of movement of the surface of the drum, all the movable clamping elements are located in the first position and, during each rotation of the drum, each movable clamping element effects a translational movement from the first position to the second position at a velocity less than the tangential velocity of the surface of the drum;

a supply source which can supply the continuous elastic web to the surface of the drum at a velocity less than the difference between the tangential velocity of this surface and the velocity of the translational movement of the movable clamping elements from the first position to the second position;

second actuator means which, when the fixed and movable clamping elements provided on the rotary drum move through the predetermind region of the path of movement of the surface of the drum, can close the clamping elements on the web supplied by the source, and a cutting element which can cut the continuous web in correspondence with predetermined region of the path of movement of the surface of the drum; the operation of the first actuator means, the second actuator means, and the cutting element being synchronised with the rotational movement of the drum, in order to effect the cyclic sequence of operations including, in order:

the drawing of the free end of the web by the movable clamping element while this movable clamping element moves from the first position to the second position so that, as a result of this drawing, a state of tension is imparted to the portion of the web between the supply source and movable clamping element, the degree of which is determined by the difference between the tangential velocity of the surface of the drum and the translational velocity of the movable clamping element from the first position to the second position and the supply velocity of the web;

the clamping of the web in the fixed clamping element downstream of the movable clamping element in the direction of movement of the surface of the drum when the movable clamping element reaches the second position, with the consequent formation between the movable clamping element and the downstream fixed clamping element of a piece of web in the said state of tension;

the clamping of the web in a further movable clamping element located in the said first position adjacent the fixed clamping element, and the operation of the cutting element to cut that portion of the web between the fixed clamping element and the further movable clamping element adjacent thereto, in order to cause the separation from the main body of the web of the piece defining one of the tensioned elastic elements and the formation of a new free end of the web which can be drawn by the further movable clamping element.

Figure 2:
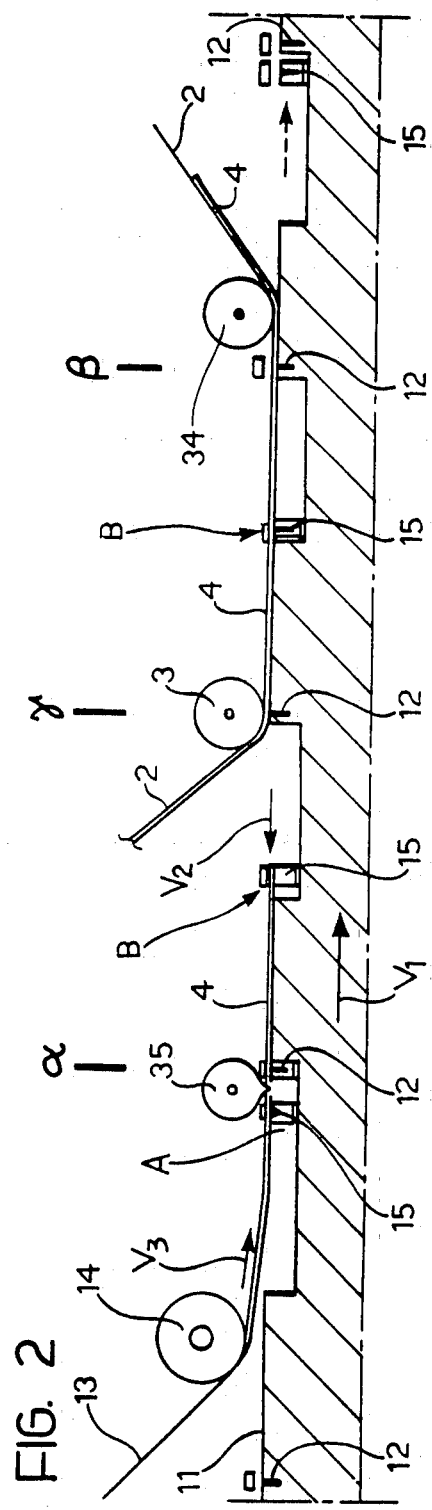
Figure 3:
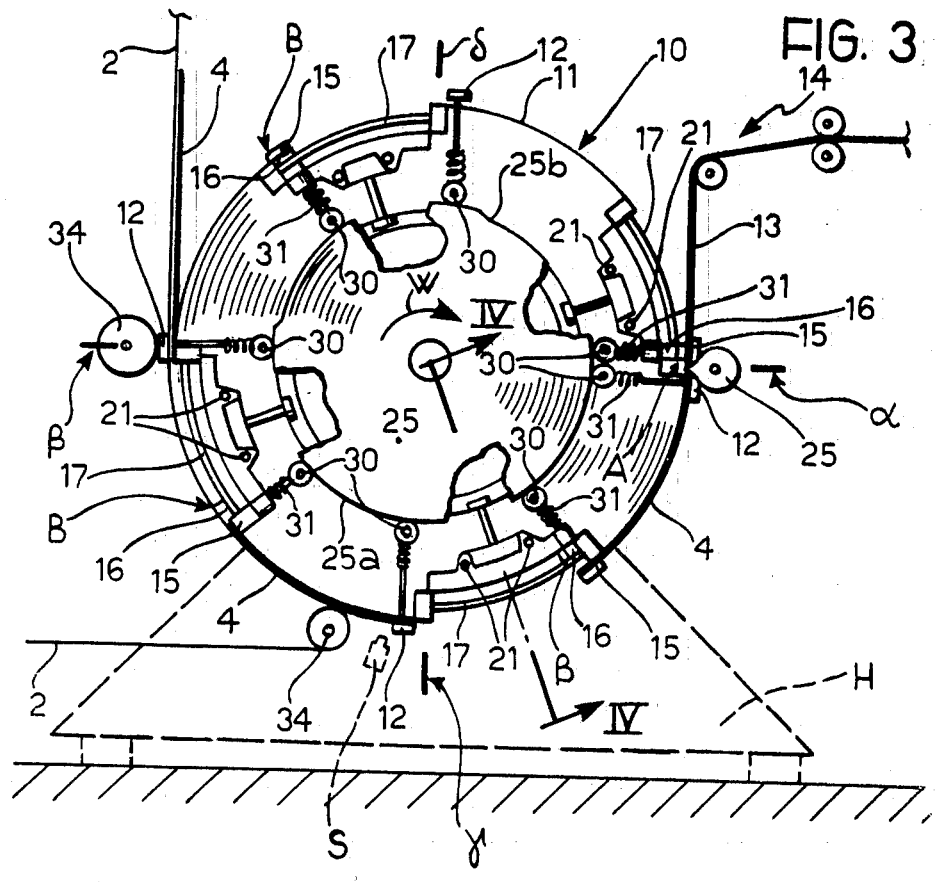
Figure 4:
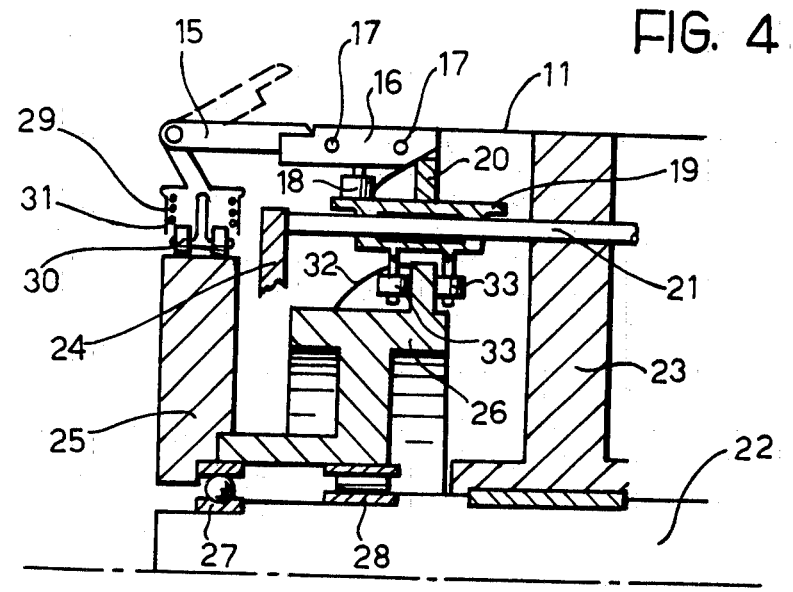

The invention will now be described, purely by way of non-limiting example, with reference to the appended drawings, in which:

FIG. 1 illustrates schematically a disposable diaper for infants or incontinent adults, which can be manufactured by the method and apparatus according to the invention, FIG. 2 illustrates schematically the method of the invention FIG. 3 illustrates the basic elements of the apparatus of the invention, FIG. 4 is a section taken on the line IV—IV of FIG. 3, and FIGS. 5 to 7 illustrate schematically the criteria which govern the operation of several of the elements illustrated in FIGS. 3 and 4.

In FIG. 1, a disposable absorbent diaper for infants or incontinent adults is generally indicated 1.

The diaper 1 is constituted essentially by a sheet 2 of impermeable plastics material, for example a polyethylene film having a thickness of 25-30 microns.

To the sheet 2, which is approximately rectangular, is applied an absorbent body 3 of elongate form constituted by a wad of dry ground cellulose or like material.

Although retaining a generally elongate form, the absorbent body 3 may however have different shapes from that shown in FIG. 1, for example an anatomical shape with end parts which are wider than the central area.

Two elastic strip elements 4 are glued to the sheet 2 along the longer edges of the absorbent body 3.

The longer sides of the impermeable sheet 2 have central parts which are curved inwardly and define the so-called leg portions of the diaper, that is, the portions of the edge which will surround a user's legs.

The elastic elements 4 are supplied to the impermeable sheet 2 in a state of tension; the resilient contraction force they exert causes the diaper 1 to curve into an anatomical bowl shape which helps the flow of physiological liquids to the absorbent body 3.

The diaper is secured around the user's waist by interconnecting the shorter sides of the impermeable sheet 2 constituting the outer covering of the diaper at their ends by means of the usual adhesive tabs, indicated 5.

The absorbent body 3 is normally fixed to the impermeable sheet 2 by a further fluid-permeable covering sheet, indicated 6. The covering sheet 6, which is intended to come into contact with the user's skin, is preferably made from a non-woven fabric so as to minimise the irritation resulting from chafing against the user's skin.

The elastic elements 4 are fixed to the impermeable body 2 by an adhesive strip of hot-melt material, the setting time of which is quick enough to allow the elastic elements 4 to be applied to the impermeable sheet 2 at the high rate used in industrial production.

FIGS. 2 to 7 illustrate schematically apparatus for use in the formation of elastic elements 4 in the method of manufacture of the diaper of FIG. 1.

More particularly, in FIG. 3, a drum, generally indicated 10, is rotated in a clockwise sense by drive means, not illustrated. The outer surface of the drum 10, indicated 11, is illustrated schematically in a rectilinear development in FIG. 2.

First jaws 12 for clamping a web 13 of rubber or similar elastic material to the outer surface of the drum are mounted in equiangularly distributed positions on the outer surface 11 of the drum 10. The web 13 is supplied continuously to the drum from a supply source illustrated schematically as a group of motor-driven pulleys or rollers, generally indicated 14.

The velocity at which the web 13 is supplied from the source 14 may be controlled precisely, in the manner which will be explained in greater detail below.

The jaws 12, of which there are four, are located at 90° to each other around the perimeter of the drum 10 and may be of any known type, for example of the type illustrated in the U.S. Pat. No. 4,297,157 mentioned above.

Four further jaws for clamping the web 13, indicated 15, are mounted on the outer surface of the drum 10 in alternation with the jaws 12.

With regard to the manner of operation and particularly the clamping of the web 13, the jaws 15 are substantially similar to the jaws 12.

However, while the jaws 12 are fixed to the drum 10, each of the jaws 15 (FIGS. 4 to 7) is mounted on a support carriage 16 which can effect a translational movement along the surface 11 of the drum 10 on profiled sliding guides 17 which are typically arcuate and extend tangentially relative to the drum 10 in planes perpendicular to the axis of the drum 10 itself.

As a result of the sliding of the support carriages 16 along the guides 17, each jaw 15 can effect a translational movement along the surface 11 of the drum 10 between two extreme positions indicated A and B respectively in FIGS. 2 and 3.

More particularly, in FIG. 3, only one jaw 15 is illustrated in the first position A while the other three jaws 15 are illustrated in the second position B.

In FIG. 2, which, as mentioned above, shows an ideal linear development of the surface of the drum 10, a jaw 15 in the first position A is shown on the left-hand side, two jaws 15 in the second position B are shown in the centre, and a jaw 15 which is returning to the first position A from the position B is shown on the right-hand side.

In the first position, each jaw 15 (movable jaw) is immediately behind the jaw 12 (fixed jaw) preceding it in the direction of movement of the surface 11 of the drum 10.

In the rectilinear development of FIG. 2, this movement is shown as developing from left to right.

In the second position B, each movable jaw 15 is in a position intermediate the fixed jaws 12 between which it is positioned.

The length of the guides 17, that is, the amplitude of the movement of the movable jaws 15 between the first position A and the second position B, is selected so that, in the second position B, the distance between each movable jaw 15 and the fixed jaw 12 which it follows in the direction of movement of the outer surface 11 of the drum 10 is substantially identical to the length of the tensioned elastic elements to be formed.

In the present description and in the following claims, the terms "upstream" and "downstream" are used for the relative positions of the jaws 12 and 15 on the surface 11 of the drum 10, with reference to the direction of movement of the surface acting as a support for the formation of the elastic elements 4. More particularly, of two adjacent jaws which pass successively in front of the group of pulleys 14 which supply the web 13, the first jaw is termed the "upstream" jaw while the other jaw is termed the "downstream" jaw. Hence, with reference to the development of FIG. 2, each jaw illustrated in this drawing is "upstream" of the jaws to its left and "downstream" of the jaws to its right.

Each support carriage 16 has a pair of rollers or bearings 18 beneath in which cooperate with the opposite faces of a rib provided on the radially outer face of a drive carriage 19 underlying it (in a radial direction relative to the drum 10).

This rib, indicated 20 in the drawings, has a generally arcuate course which follows the curvature of the drum 10 and extends in a plane inclined at about 45° to the planes containing the guides 17. The rib 20 constitutes a ramp part for causing the translational movement of the support carriage 16 along the guides 17 as a result of the translation of the drive carriage 19 axially relative to the drum 10.

In a structurally similar disposition to that of the support carriages 16, each drive carriage 19 is movable along straight guides 21 which extend axially relative to the drum 10.

In the embodiment illustrated, there are eight guides 21 (two for each drive carriage 20) and these are mounted on the drum 21 in angular positions intermediate the ends of the path of movement of the support carriage 16 on the guides 17.

The internal structure of the drum 10 is illustrated in greater detail in FIG. 4. In this drawing, the reference 22 indicates a horizontal-axis drive shaft on which is rigidly keyed a disc 23 (or functionally equivalent element such as a ring) supporting the outer surface 11 of the drum 10 on its free edge. This surface is normally constituted by a curved sheet-metal plate possibly treated with a non-stick material, such as a silicone rubber, for reasons which will be better explained below.

The guides 21 extend between the disc or ring (rotor) 23 and the front surface of the drum 10 in correspondence with which the movable jaws 15 and the fixed jaws 12 aligned therewith act.

At their ends opposite the rotor 23, the guides 21 are connected by a stiffening element 24 which is also rotated by the shaft 22.

Two annular elements, indicated 25 and 26, are fitted onto the drive shaft 22 with the interposition of bearings 27 and 28, but are not free to rotate relative to the shaft 22 itself.

More particularly, the annular elements 25 and 26, which are rigid with each other, are connected by fixing means, not illustrated, to the support frame of the drum 10, schematically indicated H in FIG. 3. These are therefore stationary relative to the drum 10 and may act easily as support elements for the shaft 22.

The annular elements 25 and 26 have profiled peripheral edges which act as operating cams for the jaws 12, 15 and for the carriages 16 supporting the movable jaws 15.

In the embodiment illustrated, the operation (opening-closing) of the jaws 12 and 15 is effected by the movement of movable units 29, one of which is illustrated schematically in FIG. 4 and each of which has a feeler roller 30 which rolls on the peripheral edge of the annular element 21 against which it is urged by a spring 31.

More particularly, when the roller 30 is thrust outwardly of the drum 10, the corresponding jaw 12 or 15 is opened, as shown schematically in broken outline in FIG. 4 with reference to a movable jaw 15. In its open position, each jaw 12, 15 can receive the web 13 supplied from the supply station 14 or, as will be better seen below, allow the removal of a web piece constituting one of the tensioned elastic elements to be formed from the surface of the drum 10. When the feeler roller is returned to the drum 10 under the action of the spring 31, the corresponding jaw 12, 15 closes to clamp the web 13 onto the surface of the drum 10.

As schematically illustrated in FIG. 3, the peripheral edge of the annular element 25 comprises two consecutive semicircular portions concentric with the drum 10. One of these portions, indicated 25a, has a larger radius and extends in correspondence with the lower half of the circular path of movement of the outer surface of the drum 11 between two angular positions schematically indicated α and β in FIG. 3.

The other edge portion of the element 25, indicated 25b, extends between the angular positions α and β in correspondence with the upper half of the circular path of movement of the surface of the drum 10. Thus, the arrangement is such that, during the rotation of the drum 10, the jaws 12, 15 which are momentarily in the lower portion of the path of movement of the surface 11 are in a clamped or closed position, while the jaws 12, 15 which are in the remaining portion of this path are open.

For an easier understanding of the invention, references indicative of the developed relative locations of the angular positions α and β are given in FIG. 2.

From the peripheral edge of the annular element 26 projects a profiled rib the opposite sides of which constitute rolling surfaces for a pair of bearings 33 mounted on the radially inner face of each drive carriage 19 in a disposition substantially similar to that adopted by the bearings 18 of the support carriage 16.

As is partially visible in FIG. 4, the rib 32, which extend in continuity with the outer edges of the annular element 26, includes portions disposed in different orthogonal planes to the drive shaft 22 and inclined portions which connect these portions orthogonal to the shaft 22.

The rib 32 thus constitutes a cam which controls the axial translational movement of the drive carriages 19 along the guides 21, and consequently the translational movement of the carriages 16 supporting the movable jaws 15, between the positions A and B defined above.

Figure 7:
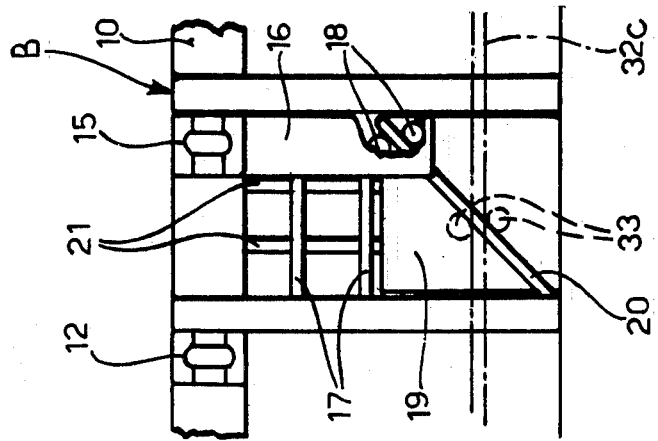
Figure 6:
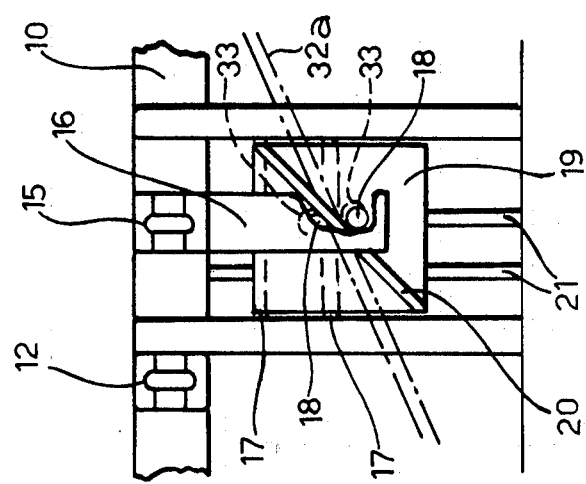
Figure 5:
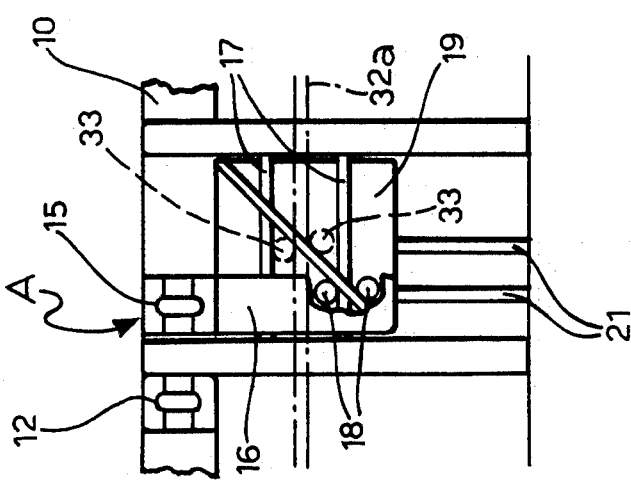

The action fulfilled by the rib 32 is illustrated schematically in FIGS. 5 to 7.

In the position illustrated in FIG. 5, which relates to a possible relative disposition assumed by a support carriage 16 and its drive carriage 19 in a portion of the path of rotation of the surface 11 of the drum 10, the rollers 33 of the drive carriage 19 engage a portion 32a of the rib 32, which lies in a plane normal to the axis of rotation of the drum 10. The axial position of this plane relative to the drum is such that the drive carriage 19 is in the position of maximum advancement towards the front surface of the drum itself, and the corresponding support carriage 17 is in a position which, purely by way of example, has been made to correspond with the location of the jaw 15 supported by the carriage in the first position A.

FIG. 6 illustrates a situation in which, as a result of the rotation of the drum 10, the rollers 33, which are only partially visible in the drawing since they are shown in broken outline engage an inclined portion 32b of the rib 32, that is, a portion of the rib 32 which is moving gradually away from the frontal face of the drum 10. Under these conditions, the drive carriage 19 also moves away from the front surface, while the rollers 18 of the support carriage 16 slide along the rib 20, gradually drawing the support carriage 16 towards the other end position of its translational movement along the guides 17.

Finally, FIG. 7 illustrates a situation in which, as a result of the further rotation of the drum 10, the rollers 33 slidingly engage a further portion of the rib 32, indicated 32c, which lies in a plane normal to the axis of rotation of the drum. In this case, the axial position of this plane relative to the drum 10 is such that the drive carriage 19 driven by the rollers 33 is in the position of maximum withdrawal relative to the frontal face of the drum 10.

Under these conditions, the rollers 18 have completed their course of sliding movement along the rib 20, carrying the support carriage 10 and the movable jaw 15 mounted thereon into the travel limit position indicated B.

From what has been described in outline with reference to FIGS. 5 to 7, one may easily understand how the rib 32 may be profiled so as to obtain any law of movement of the carriages 16 along the surface 11 of the drum 10.

In FIG. 3, γ and δ indicate two further angular positions of the path of rotation of the surface of the drum 10. These angular positions are diametrally opposed in a direction perpendicular to the direction of alignment of the angular positions α and β previously defined.

FIG. 2 shows approximately the location of the angular position γ in the rectilinear development of the surface of the drum 10.

In the embodiment illustrated, the rib 32 provided on the peripheral edge of the tubular element 26 has a profile such that all the support carriages 16 and their movable jaws 15 are in the first position A in correspondence with the angular position α, and move gradually towards the second position B during the advance from the angular position α to the angular position γ caused by the rotation of the drum 10.

In the portion of the path of movement of the surface of the drum 10 between the angular positions γ and β, the support carriages 16 and their movable jaws 15 are held in the second position B.

Two rollers, indicated 34, are located in positions substantially tangential to the roller 20 in correspondence with this path portion. A continuous sheet of impermeable plastics material indicated 2 by analogy with FIG. 1, unwinds between the rollers 34.

The sheet portion 2 between the rollers 34 adheres to the outer surface 11 of the drum 10 and is drawn thereby as a result of the rotation of the drum itself.

Before its supply to the drum 10, an adhesive, for example a hot-melt adhesive, is applied to the sheet 2 so as to form a firm connection between the sheet 2 and the elastic web pieces 13 which are brought into contact therewith in the manner which will be described more fully below.

The application of the hot-melt adhesive to the sheet is carried out at a spreading station, not shown in the drawings. As a possible alternative, the hot-melt adhesive may be applied to the elastic web 13 by a spreading device which acts on the elastic web 13 adjacent to the angular position γ.

This spreading device is illustrated schematically in broken outline and indicated S in FIG. 3.

Since, as illustrated in FIG. 1, each diaper 1 has two elastic elements 4 disposed parallel to each other on opposite sides of the absorbent body 3, in its application to the manufacture of these products the apparatus according to the invention includes two structures for forming elastic elements which are identical to each other and operate in parallel. For example, it is possible to provide a configuration of fixed jaws 12 and movable jaws 15 (with their drive means and the feed for the web) similar to that described above on both frontal faces of the rotary drum 10.

For obvious reasons of simplicity in the present description, only the members which effect the application of one of the elastic elements 4 are shown, since the application of the other elastic element is achieved in exactly the same way.

Downstream of the angular position β in the direction of movement of the surface of the drum 10, the support carriages 16 and the movable jaws 15 mounted thereon are carried gradually towards the first position A.

In the embodiment illustrated, the rib 32, acting as an operating cam for the carriages 16 and 19, is profiled so that the carriages 16 and the jaws 15 remain in the position B until the angular position δ is reached, and then turn to the first position A during the advance along the arc of the path of movement of the surface of the drum between the angular position δ and the angular position α, returning to the initial conditions described above.

It should be stressed that the relative disposition of the angular positions indicated α, β, γ, and δ illustrated in FIG. 3 (a uniform angular distribution with a spacing of 90°) is purely by way of example as a proposed solution which is of particular advantage when four fixed jaws 12 and four movable jaws 15 project from the surface of the drum 10. Depending on the application or requirements, a different disposition may of course be used, particularly when there is a different number of fixed and movable jaws on the outer surface of the drum 10.

Finally, a cutting element 35, for example a rotary blade, is shown which acts on the elastic web 13 applied to the surface of the drum 10 in correspondence with the angular position α. More specifically, the cutting element 35 can act on the web portion 13 between each fixed jaw 12 and the movable jaw 15 downstream of this fixed jaw 12, when the two jaws pass through the angular position α as a result of the rotation of the drum 10. As indicated above, under these conditions, the movable jaw 15 is in the first position A.

The cutting member 35 is intended to section the continuous web 13, cutting tensioned web pieces constituting the elastic elements 4 to be applied to the plastics sheet 2 from the continuous body of the web 13.

The operation of the apparatus according to the invention is effected by rotating of the drum 10 and operating of the supply source for the web 13 (shown schematically as the rollers 14) and the cutting member 35 simultaneously and continuously. As a result of the presence of the annular elements 25, 26 acting as drive cams, the rotation of the drum 10 drives the closing and opening of the jaws 12 and 15, and the reciprocating movement of the jaws 15 between the first position A and the second position B, as explained above.

The values chosen for the translational velocity of the movable jaws 15 and the supply velocity of the elastic web 13 from the source 14, in dependence on the velocity of rotation of the drum 10, are of paramount importance for the carrying out of the invention.

By way of example, it is assumed that the drum 10 has a rotational velocity $\omega_1$ such that the outer surface 11 of the drum 10 moves in a clockwise sense with a tangential velocity $V_1$.

The portion of the rib 32 between the angular positions α and β, which acts as a drive cam for the carriages 16 on which the jaws 15 are mounted, has a profile such that the translational movement of the jaws 15 between the position A and the position B is effected at a velocity $V_2$ (relative to the surface 11 of the drum 10) which is less than the velocity $V_1$ of advance imparted to the surface itself as a result of the rotation of the drum 10.

The translational velocity of the jaws 15 from the first position A to the second position B is in the opposite direction from that of the velocity $V_1$, as shown schematically by the respective arrows in FIG. 2.

The superposition of the rotational movement of the drum 10 on the movement of the jaws 15 from the first position A to the second position B means that, while the surface 11 of the drum 10 travels with a tangential velocity $V_1$ through the arc between the angular position α and the angular position γ, the jaws 15 mounted thereon have a tangential velocity equal to $V_1-V_2$ and thus travel only through a part of this arc.

More particularly, the value of the velocity $V_2$ is chosen so that (see FIG. 3) each movable jaw 15 reaches the second position B having left the first position A exactly when the fixed jaw 12 located downstream in the direction of advance of the surface of the drum reaches the angular position in which the cutting member 35 acts.

With reference to the embodiment illustrated, the second position B of the movable jaws 15 is chosen so that, in this second position, each movable jaw 15 is in a median position relative to the fixed jaws 12 between which it is positioned. The profile of the rib 32 is thus selected so that the value of the velocity $V_2$ is equal to half the value of the tangential velocity $V_1$ of the surface of the drum 10.

Thus, it is possible, while the surface of the drum 10 advances through an arc of 90° between the angular positions α and γ, to make the movable jaw 15 mounted thereon advance through an arc of only 45°, that is, an arc equal to half the arc travelled by the surface of the drum 10.

Naturally, after reaching the second position B halfway between the angular positions α and γ, each movable jaw 15 stops moving translationally relative to the drum 10 and is drawn thereby at the velocity $V_1$.

With regard to the supply velocity of the web 13 from the source 14, the velocity indicated $V_3$, this is chosen so as to be less than the difference between the tangential velocity $V_1$ of the surface 11 of the drum 10 and the translational velocity $V_2$ of the jaws 15 from the first position A to the position B. This difference ($V_1-V_2$) determines the velocity at which each movable jaw 12 passes through the initial portion of the arc between the angular position α and the angular position intermediate the positions α and γ at which the jaw 15 itself reaches the second position B. With reference to the choice of values indicated above, $V_2$ is equal to half $V_1$ whereby this difference is also equal to half $V_1$.

The fact that a value of the web supply velocity is chosen to be less than the velocity difference means that the web 13 is applied to the surface of the drum 10 under tension.

The degree of this tension is determined by the ratio between the velocity difference $V_1-V_2=\frac{1}{2}V_1$ and the web supply velocity $V_3$. More particularly, in the currently preferred embodiment, by selecting a supply velocity value $V_3$ for the web which is equal to $\frac{1}{4}V_1$, it is possible for the web 13 to be applied to the surface of the drum 10 in a state of tension equal to 100%, that is, a state in which a unitary element of the tensioned web has a length equal to twice its rest length.

The sequence of operations of the apparatus according to the invention will now be explained with specific reference to FIG. 2. This drawing may be interpreted as a linear development of the disposition assumed at a predetermined instant by the jaws 12, 15 disposed on the surface of the drum 10, and as an illustration of a chronological sequence of the positions reached successively by a single fixed jaw-movable jaw unit.

At its left-hand side, FIG. 2 illustrates the relative positions assumed by a movable jaw 15 and the fixed jaw 12 located downstream thereof in the direction of advance of the surface 11 of the drum when the web 13 is clamped in the movable jaw 15 which is located in the first position A in correspondence with the position α.

The web piece 13 which is clamped in the movable jaw 15 corresponds, in fact, to the free end of the web 13 itself in that, immediately upstream of the jaw 15, the cutting member 35 cuts the web 13 to separate a piece of web formed previously in the manner which will now be described.

Immediately the surface 11 of the drum passes through the angular position α at a tangential velocity $V_1$, the movable jaw 15 starts to move on the surface 11 towards the second position B at a velocity $V_2$ the value of which, as indicated above, is equal to half the value of the tangential velocity $V_1$.

Under these conditions, the end of the web 13 clamped in the jaw 15 advances relative to the source 14, which is stationary, at a velocity equal to the difference $V_1-V_2$, that is, at a velocity equal to half $V_1$.

The web 13 is supplied at a velocity equal to a quarter of $V_1$, that is, at a velocity less than the difference $V_1-V_2$. The web portion 13 between the movable jaw 15 and the source 14 is thus stretched longitudinally, which puts it under tension. With the velocity values indicated above ($V_1-V_2=2V_3$) the web 13 is stretched by 100% and, being under tension, has a length equal to twice the relaxed length. As illustrated schematically in the central part of FIG. 2, the movable jaw 15 reaches the position B at half the arc of the path between the angular positions α and γ exactly when the fixed jaw 12 located downstream thereof reaches the angular position α together with a further movable jaw 15 which has just returned to the first position A. Under the action of cam 25, the fixed jaw 12 and the further movable jaw 15 close on the web supplied by the source 14. Between the fixed jaw 12 and the movable jaws 15 located upstream in positions intermediate the positions α and γ, there is thus formed a tensioned web piece which can be applied to the sheet 2. This piece is separated from the main body of the web 13 by the cutting member 35 which acts on the web portion between the fixed jaw 12 and the further movable jaw located immediately downstream.

The cutting member 35 thus forms a new free end of the web 13 destined to be drawn at the velocity $V_1-V_2$ by the further movable jaw during the cycle of formation of a new tensioned elastic piece.

The tensioned elastic piece which has just been formed, of which the ends are clamped between the movable jaw 15 and the fixed jaw 12, advances towards the angular position at a tangential velocity $V_1$.

In the manner briefly described above, in the arc between the angular positions γ and β, the piece is stuck to the plastics sheets 2 as an electric element 4 which can confer elasticity and greater adherence to the diaper.

When the adhesive has set (typically around the angular position indicated β), the jaws 15 and 12 clamping the ends of the elastic element open and the plastics sheet 2 is removed from the surface 11 of the drum 10, drawing with it the elastic elements 4 applied thereto.

As indicated above, at least those portions of the surface 11 of the drum 10 for conveying the web pieces 13 are preferably coated with a resilient material, such as a silicone rubber, in order to facilitate the detachment of the sheet 2 carrying the applied elastic elements 4 from the drum 10 itself.

In the end part of the path of movement of the surface 11, between the angular position δ and α, the movable jaw 15 returns to the first position A to receive the web 13 again and to start a new cycle of formation of an elastic element 4.

In the embodiment illustrated in FIG. 3, four equiangularly spaced-apart fixed jaw-movable jaw units are provided on the surface of the drum. In the development of the surface of the drum 10 between the angular position α and the angular position γ, it is thus possible to see a unit in which a tensioned elastic piece has just been formed. The rear end (in the direction of translational movement of the surface of the drum) of the piece is separated from the main body of the web 13 by the cutting member 35.

Between the angular positions α and β, however, there can be seen the other unit which pulls a tensioned elastic piece causing it to stick to the plastics sheet 2 unwinding from the rollers 34.

Between the angular positions β and δ, there can be seen a unit in which the fixed jaw 12 is open, as is the movable jaw 15 preceding it, to allow an elastic piece 4 firmly applied to the sheet 2 to move away from the drum.

Finally, between the angular positions δ and α, there can be seen a unit in which the movable jaw 15 has returned to the first position A to receive the new free end of the web 13. This new free end is formed by the element 35 during the cutting operation which separates the tensioned the elastic piece just formed in the unit located between the angular positions α and γ from the main body of the web 13.

A method and apparatus are thus described which allow the rapid formation of tensioned elastic elements, in a manner which can be achieved practically and economically on an industrial scale, it being possible to stick these tensioned elastic elements to a support such as a sheet of impermeable plastics material forming the outer covering of a sanitary product such as a disposable diaper.

More particularly, it may be seen that the invention allows the formation of tensioned elastic elements while avoiding the disadvantages typical of the prior art.

More particularly, the elastic elements formed according to the invention can be stuck to an inelastic support avoiding the wastage of material resulting from the formation of tails which will return to the rest condition after application.

Furthermore, in no stage of the method for the formation of the elastic elements is the material of the web subjected to tensions greater than that needed for application to the final product. Thus, the typical disadvantages resulting from over-stretching of the elastic web during working are avoided.

Naturally, the principle of the invention remaining the same, the constructional details and forms of embodiments may be varied widely with respect to that described and illustrated, without thereby departing from the scope of the present invention.

What is claimed is:

1. A method for forming elastic elements under tension from a continuous elastic web, including the steps of:
   providing a supply source of the web;
   providing a support for fixing the elastic elements, having a clamping element fixed to the support and a further clamping element movable relative to the fixed element between a first position and a second position; the distance between the fixed clamping element and the movable clamping element in the second position being less than the distance in the first position and substantially equal to the length of the tensioned elastic elements;
   clamping the free end of the continuous web in the movable clamping element in the first position;
   causing, simultaneously and substantially continuously,
   (a) a relative movement between the supply source and the support in the direction of alignment of the clamping elements so as to cause the supply of the continuous web to the fixed clamping element,
   (b) the translational movement of the movable clamping element from the first position to the second position at a velocity less than the velocity of the relative movement between the supply source and the support, and
   (c) the supply of the web from the source at a velocity less than the difference between the velocity of the relative movement between the source and the support and the velocity of the translation of the movable clamping element from the first position to the second position;
   clamping of the web in the fixed clamping element when the movable clamping element reaches the second position, in an arrangement such that a piece of web defining one of said elastic elements extends between the fixed clamping element and the movable clamping element in a state of longitudinal tension the degree of which is determined by the velocity difference and the supply velocity of the web, and
   cutting the web in the region between the fixed clamping element and the supply source to separate the tensioned piece from the main body of the web and form a new free end of the web.

2. A method as defined in claim 1, including the steps of:
   providing a supply source for the continuous web;
   providing a support movable relative to the supply source at a predetermined velocity and carrying associated fixed and movable clamping elements which are aligned in alternation in the direction of movement of the support, each of the movable clamping elements being able to effect a reciprocating translational movement between a first position substantially adjacent the fixed clamping element upstream of the movable element in the direction of movement of the support and a second position intermediate the upstream fixed clamping element and the downstream fixed clamping element in the direction of movement;
   clamping the free end of the continuous web in one of the movable clamping elements in the first position;
   driving the translational movement of the movable clamping element carrying the clamped free end of the web from the first position to the second position at a velocity less than the velocity of movement of the support, and simultaneously supplying the continuous web to the support at a velocity less the difference between the velocity of movement of the support and the translational velocity of the movable element between the first and second positions;
   clamping the web in the fixed element located downstream of the movable element in the direction of movement of the support when the movable clamping element reaches the second position, in an arrangement such that a piece of web defining one of the elastic elements extends between the movable clamping element and the fixed clamping element located downstream in a state of tension the degree of which is determined by the velocity difference and the supply velocity of the web;
   clamping the web in a further movable clamping element located in the first position downstream of the fixed clamping element in the direction of movement of the support, and
   cutting the web in the region between the fixed clamping element and the further movable clamping element to separate the tensioned piece from the main body of the web and form a new free end of the web clamped in the further movable clamping element and defining one of the ends of a new elastic element.

3. A method as defined in claim 1, wherein the translational velocity of each movable clamping element between the first and second position and the supply velocity of the web are chosen to be about half and about a quarter, respectively, of the velocity of the relative movement of the supply source for the web and the support, whereby the web pieces defining the tensioned elastic elements have a length substantially equal to twice their rest length.

4. Apparatus for forming tensioned elastic elements from a continuous elastic web, comprising:

a rotary drum having first clamping elements fixed to the drum and second movable clamping elements aligned in alternation along the outer surface of the drum, each of the movable elements being able to effect a reciprocating translational movement between a first position substantially adjacent the fixed clamping element located upstream in the direction of movement of the surface of the drum and a second position in which each movable clamping element is located in a position intermediate the fixed clamping elements between which it is interposed at a distance from the fixed clamping element located downstream in the direction of movement of the surface of the drum substantially equal to the length of the elastic elements;

first actuator means which can move the movable clamping elements in a disposition such that, in a predetermined region of the path of movement of the surface of the drum, all the movable clamping elements are located in the first position and, during each rotation of the drum, each movable clamping element effects a translational movement from the first position to the second position at a velocity less than the tangential velocity of the surface of the drum;

a supply source which can supply the continuous elastic web to the surface of the drum at a velocity less than the difference between the tangential velocity of this surface and the velocity of the translational movement of the movable clamping elements from the first position to the second position;

second actuator means, which, when the fixed and movable clamping elements provided on the rotary drum move through the predetermined region of the path of movement of the surface of the drum, can close the clamping elements on the web supplied by the source and a cutting element which can cut the continuous web in correspondence with predetermined region of the path of movement of the surface of the drum, the operation of the first actuator means, the second actuator means, and the cutting element (35) are synchronised with the rotational movement of the drum, to effect a cyclic sequence of operations including, in order:

the drawing of the free end of the web by the movable clamping element while this movable clamping element moves from the first position to the second position so that, as a result of this drawing, a state of tension is imparted to the portion of the web between the supply source and movable clamping element, the degree of which is determined by the difference between the tangential velocity of the surface of the drum and the translational velocity of the movable clamping element from the first position to the second position and the supply velocity of the web;

the clamping of the web in the fixed clamping element downstream of the movable clamping element in the direction of movement of the surface of the drum when the movable clamping element reaches the second position, with the consequent formation between the movable clamping element and the downstream fixed clamping element of a piece of web in the said state of the clamping of the web in a further movable clamping element located in the said first position adjacent the fixed clamping element, and the operation of the cutting element to cut that portion of the web between the fixed clamping element and the further movable clamping element adjacent thereto, in order to cause the separation from the main body of the web of the piece defining one of the tensioned elastic elements and the formation of a new free end of the web which can be drawn by the further movable clamping element.

5. Apparatus as defined in claim 4, wherein the velocity of translational movement of the movable clamping elemnts from the first position to the second position and the supply velocity of the web are chosen to be about a half and about a quarter, respectively, of the tangential velocity of the surface of the rotary drum, whereby the pieces defining the tensioned elastic elements have a length substantially twice their rest length.

6. Apparatus as defined in claim 4, wherein the second actuator means include a cam element which is stationary relative to the drum and cooperates slidingly with the clamping elements.

7. Apparatus as defined in claim 4, wherein the cam element has a profile including consecutive circular arcs which are concentric with the axis of rotation of the drum, the arcs having different radii of curvature in angular portions contiguous with the path of movement of the surface of the drum.

8. Apparatus as defined in claim 4, wherein or each movable clamping element, the drum has associated therewith:

sliding guides extending tangentially relative to the drum in planes normal to the axis of rotation of the drum;

a carriage for supporting the movable clamping element which is slidable along the guides;

further guides extending axially relative to the drum;

a drive carriage slidable on the further guides, and ramp elements interposed between the support carriage and the drive carriage in a position such that the translational movement of the drive carriage axially relatively to the drum causes the translational movement of the support carriage tangentially relative to the drum.

9. Apparatus as defined in claim 8, wherein one of the support carriage and the drive carriage has a surface groove facing the other carriage and the other carriage has rotary bodies in rolling cooperation with the surface groove.

10. Apparatus as defined in claim 8, wherein it includes a further cam element which is stationary relative to the drum and cooperates slidingly with the drive carriages associated with the movable clamping elements in order to cause the movement of the drive carriages axially relative to the drum.

11. Apparatus as defined in claim 10, wherein the further cam element has a peripheral rib the course of which defines the cam profile, and the drive carriages have associated rotary bodies in rolling cooperation with the peripheral rib.

* * * * *